United States Patent
Gröber et al.

(10) Patent No.: US 8,105,277 B2
(45) Date of Patent: Jan. 31, 2012

(54) DEVICE AND METHOD FOR MONITORING A VASCULAR ACCESS, AND DEVICE FOR CREATING A VASCULAR ACCESS

(75) Inventors: Tobias Gröber, Heusenstamm (DE); Christoph König, Wiesbaden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 104 days.

(21) Appl. No.: 12/438,822

(22) PCT Filed: Aug. 31, 2007

(86) PCT No.: PCT/EP2007/007610
§ 371 (c)(1),
(2), (4) Date: Feb. 25, 2009

(87) PCT Pub. No.: WO2008/028594
PCT Pub. Date: Mar. 13, 2008

(65) Prior Publication Data
US 2010/0016809 A1    Jan. 21, 2010

(30) Foreign Application Priority Data
Sep. 2, 2006    (DE) .......................... 10 2006 041 265

(51) Int. Cl.
*A61M 5/00*    (2006.01)
(52) U.S. Cl. .......................... 604/117; 604/111; 604/507
(58) Field of Classification Search .................. 604/111, 604/117, 507; 600/547; 324/692
See application file for complete search history.

(56) References Cited

U.S. PATENT DOCUMENTS

| | | | | |
|---|---|---|---|---|
| 4,585,444 | A | * | 4/1986 | Harris ........................... 604/177 |
| 5,885,251 | A | * | 3/1999 | Luther .......................... 604/161 |
| 2004/0254513 | A1 | | 12/2004 | Shang et al. |
| 2004/0260241 | A1 | * | 12/2004 | Yamamoto et al. ........... 604/117 |
| 2006/0224118 | A1 | * | 10/2006 | Morris et al. ............ 604/164.01 |
| 2007/0004996 | A1 | * | 1/2007 | Lovejoy et al. .............. 604/4.01 |
| 2009/0088662 | A1 | * | 4/2009 | Larsen .......................... 600/547 |

FOREIGN PATENT DOCUMENTS
CA    2312746    6/1999
(Continued)

OTHER PUBLICATIONS
International Search Report, PCT/EP2007/007610, mailed Nov. 23, 2007.
International Preliminary Report on Patentability for PCT/EP2007/007610, mailed on Apr. 15, 2009.

*Primary Examiner* — Jackie Ho
*Assistant Examiner* — Emily Schmidt
(74) *Attorney, Agent, or Firm* — Kenyon & Kenyon LLP

(57) ABSTRACT

The present invention relates to a device for creating a vascular access for extracorporeal blood treatment including an electrically conductive puncture needle with a proximal endpiece, a distal endpiece, and a base body made of electrically non-conductive material into which the distal endpiece is inserted. In a properly arranged vascular access, the base body, including an electrically conductive contact element, lies on the skin of the patient, when the puncture needle is located within the vessel of the patient. A disconnection or dislocation is detected by the impedance between the electrically conductive puncture needle and the electrically conductive contact element being measured and compared to a limit value. If the impedance measured is within predetermined limits, this indicates a properly arranged vascular access. A disconnection or dislocation of the puncture needle leads to a strong variation in the impedance.

22 Claims, 3 Drawing Sheets

FOREIGN PATENT DOCUMENTS

| | | |
|---|---|---|
| EP | 1736185 | 12/2006 |
| FR | 2622457 A | 5/1989 |
| WO | 99/26686 A | 6/1999 |
| WO | 99/29356 A | 6/1999 |
| WO | 01/68163 A | 9/2001 |
| WO | 2007/107561 A | 9/2007 |

* cited by examiner

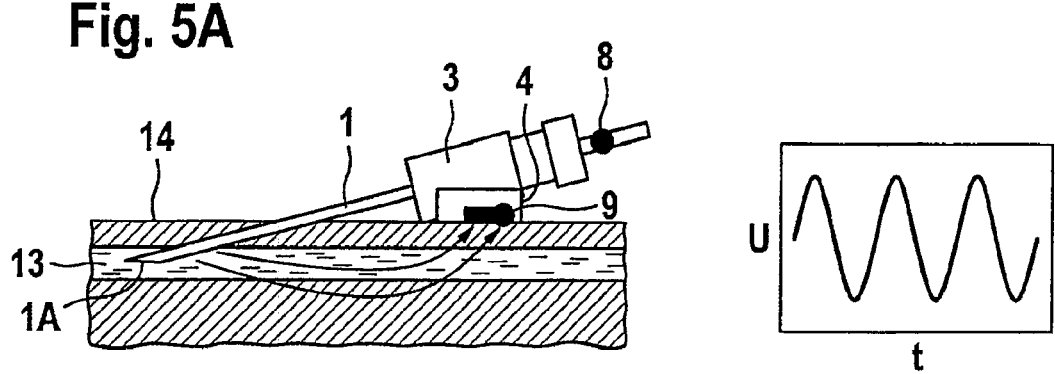
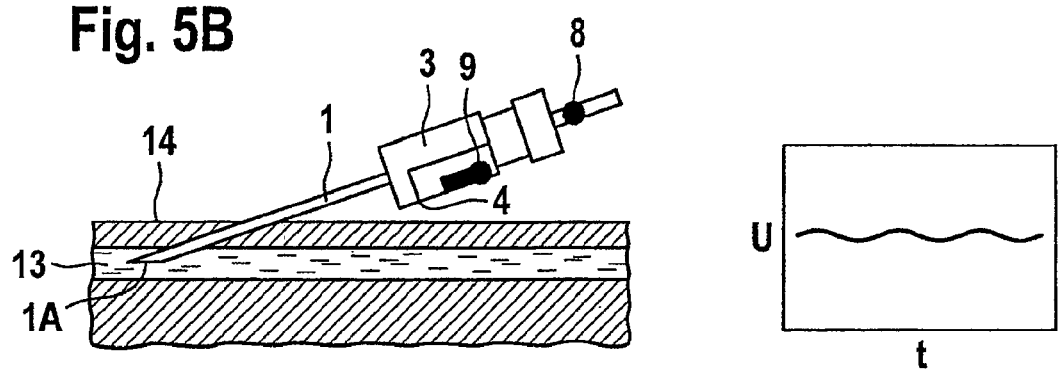
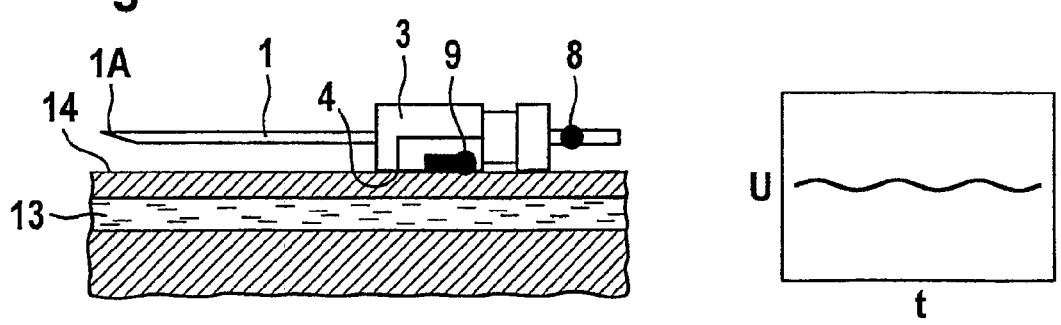

DEVICE AND METHOD FOR MONITORING A VASCULAR ACCESS, AND DEVICE FOR CREATING A VASCULAR ACCESS

CROSS REFERENCE TO RELATED APPLICATIONS

This is a 371 national phase application of PCT/EP2007/007610 filed Aug. 31, 2007, claiming priority to German Patent Application No. 10 2006 041 265.6 filed Sep. 2, 2006.

FIELD OF INVENTION

The present invention relates to a device for creating a vessel access for extracorporeal blood treatment with an extracorporeal blood treatment device. The present invention furthermore relates to a device and a method for monitoring a vessel access in the case of extracorporeal blood treatment. The present invention also relates to an extracorporeal blood treatment device with such a device.

BACKGROUND OF THE INVENTION

In the field of medical technology, various extracorporeal blood treatment devices are known that have an extracorporeal blood circulation system. The familiar extracorporeal blood treatment devices include for example dialysis machines and cell separators, both which necessitate access to the patient's vascular system. In the case of extracorporeal blood treatment, blood is removed from the patient with an arterial puncture needle via an arterial tube conduit, and is then returned to the patient via a venous tube conduit with a venous puncture needle.

Despite regular monitoring of the vessel access by hospital staff, there is a fundamental risk that the venous puncture needle could slip out of the patient's blood vessel unnoticed. If an arterial needle slips out, there may be an intake of air into the arterial tube conduit. If a venous needle slips out, however, this leads to the feared free flow of blood into the surrounding area. If it is not immediately noticed that the venous needle has slipped out, there is therefore a risk of the patient bleeding to death.

Various devices of different designs for monitoring the vessel access are known. In general, the known monitoring devices are based on the safety precautions which are standard in blood treatment appliances, and which trigger immediate interruption of the extracorporeal blood circulation in the event of incorrect vessel access.

WO 99/29356 A1 describes a monitoring device for a vessel access, in which the strength of an electrical current is measured which flows through the fluid in the tube conduit. For this, two electrodes are arranged upstream of the puncture needle, and these effect an electrical connection to the fluid in the conduit. This known monitoring device also envisages measuring the flow of electrical current between one of the electrodes and a further electrode that is placed on the patient's skin.

From US Publication No. 2004/0254513 A1, there is known an extracorporeal blood treatment device with an extracorporeal blood circulation system, which has a monitoring device for the arterial and venous vessel access. This known monitoring device has two electrodes, one of which is arranged on the arterial tube conduit and the other on the venous tube conduit, in order to produce an electrical connection between the fluid in the respective tube conduit and a monitoring unit, via two measurement lines. The monitoring unit measures the impedance between the two electrodes, with incorrect vessel access being deduced if the impedance does not lie within specified limits.

US Publication No. 2004/0254513 A1 also describes an application in infusion technology with just one tube conduit. The publication proposes providing a first electrode on the tube conduit upstream of the puncture needle to effect an electrical connection to the fluid flowing in the conduit, and providing a second electrode that is placed on the patient's skin. The monitoring unit is connected to both electrodes and monitors the strength of electrical current that flows from the first electrode on the tube conduit through the blood within the tube, the puncture needle, and that area of the patient's body between the puncture needle and the second electrode.

The devices described above have the disadvantage that producing the electrically conductive coupling points turns out to be relatively costly. Thus US Publication No. 2004/0254513 A1 in particular deals with the use of conductive polymers for producing the electrical connection to the blood in the blood tube. It is also a disadvantage that the known devices make it necessary to apply separate body electrodes.

SUMMARY OF THE INVENTION

The present invention is based on the object of monitoring a vessel access with a high degree of reliability, without extensive changes to the blood treatment device or the application of separate body electrodes. The present invention is based on the fact that the necessary electrical connections are provided solely through the device for producing a vessel access.

A first aspect of the present invention envisages a device for producing a vessel access, which has an electrically conductive puncture needle with a proximal end piece and a distal end piece and a base body of electrically non-conductive material that the distal end piece of the puncture needle is inserted into. Whilst the electrically conductive puncture needle forms the first measurement electrode, the base body has an electrically conductive contact element that forms the second measurement electrode. The puncture needle's base body, made of electrically non-conductive material, represents an insulator between the electrically conductive puncture needle and the electrical contact element.

Correct vessel access presupposes that the electrically conductive puncture needle is located within the vessel access, so that blood flows through the needle, whilst the base body with the contact element rests on the patient's arm. Defective vessel access is deduced if either the puncture needle has slipped out (disconnection) or the base body is not resting on the patient's arm (dislocation). If this is the case, the impedance between the puncture needle and the electrically conductive contact element is altered.

The device for monitoring the vessel access measures the impedance between the puncture needle and the contact element. In the event of a change in impedance outside specified limits, it concludes that there is incorrect vessel access, since incorrect vessel access leads to a marked change in impedance. The measured impedance can be compared with a threshold value or several threshold values. It is preferred that the impedance is compared to a specified lower threshold value and a specified upper threshold value, wherein incorrect vessel access is deduced if the impedance falls below the lower threshold value or exceeds the upper threshold value.

Since in general, the puncture needle consists of metal, it is possible to use a conventional puncture needle that is conductive in any case. It is however also possible to produce the puncture needle from a conductive polymer.

In a preferred embodiment, the base body of the device for producing a vessel access has a central retainer piece into which the distal end piece of the puncture needle is inserted, and two wing pieces that project away at both sides from the central retainer piece for the puncture needle. The preferred embodiment thus essentially has the design of butterfly cannulas. The two wing pieces (puncture wings) are in general of a flexible design, and are held between thumb and forefinger while piercing the vessel. After the vessel has been pierced, the puncture wings spread apart once more, so that they lie with their underside flat against the patient's skin.

In a particularly preferred embodiment, the two wing pieces include the contact element. Preferably, the contact element is provided on the underside of the two wing pieces that is to be placed on the patient, so that an electrical connection is effected between the contact element and the patient's skin. The contact element can however also be insulated with a non-conductive layer. Basically, the contact element can also be embedded in the wing pieces, for example it can be molded into the plastic wing pieces.

The design of the contact element can vary; for example, the contact element can be an electrically conductive foil or a coating of electrically conductive material. The contact element can also comprise several part-pieces that are electrically connected to one another.

In order to be able to connect the measurement lines to the monitoring unit of the monitoring device, the base body and the wing pieces preferably have two connecting pieces, with which an electrical connection to the puncture needle and the contact element can be effected.

In relation to connecting the monitoring unit of the monitoring device to the device for producing the vessel access, when two measurement lines and two connecting pieces are mentioned, this is to be understood as also meaning a common connection line with a common connection piece, which covers both connections.

A considerable advantage lies in the fact that with the exception of the connection of the measurement lines, the use of the device according to the invention for producing the vessel access requires no additional expenditure. In particular, it is not necessary to provide contact points on the tube conduits and separate contact points on the patient. In the case of the present invention, all the contact points are an integral part of the device for producing the vessel access, which preferably can form a disposable item.

In general, the device for producing the vessel access, for example in the form of a butterfly cannula, is made available as a disposable item together with the tube conduits. The necessary components for the monitoring device, to which the device for producing the vessel access is connected via the measurement lines, can in general likewise be provided without great expense, since the essential components are already present in the familiar blood treatment devices.

BRIEF DESCRIPTION OF THE DRAWINGS

A design example of the invention is explained in more detail below, with reference to the drawings. The drawings show the following:

FIGS. 5A to 5C show the voltages measured at the precision resistor of the circuit arrangement of FIGS. 3 and 4 in the case of proper patient access, dislocation, and disconnection, respectively.

DETAILED DESCRIPTION OF THE DRAWINGS

Figure 1:
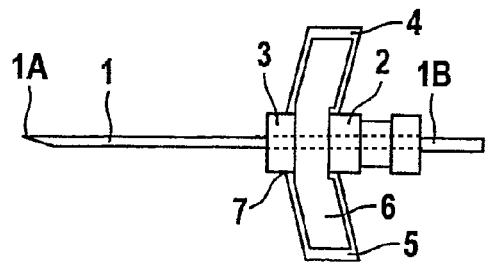
FIG. 1 shows a bottom view of a simplified schematic representation of a device according to the invention, for producing a vessel access.

The device according to the present invention for producing vessel access, which in the case of the design example described here is designed in the form of a so-called butterfly cannula, has an electrically conductive puncture needle 1 of metal, with a pointed proximal end piece 1A and a distal end piece 1B, as well as a base body 2 which is an injection-molded plastic part, into which the distal end piece 1B is inserted.

The base body 2 has a tubular central retainer piece 3, in which the distal end piece 1B of the puncture needle 1 sits. Molded onto the central retainer piece 3 for the puncture needle 1, on either side, is a flat wing piece 4, 5.

The two wing pieces 4, 5 have a flat underside 6, with which the base body 2 is placed on the patient's skin. Fitted to the underside 6 of the wing pieces 4, 5 of the base body 3 is an electrically conductive contact element 7, which is for example a layer that is formed of an electrically conductive material. The contact element 7 essentially extends over the entire underside of the wing pieces 4, 5 as well as of the base body 2.

Furthermore, the butterfly cannula has a first connecting piece 8, which is electrically connected to that section of the distal end piece 1B of the puncture needle 1 which extends beyond the base body 2, whilst a second connecting piece 9 on one of the two puncture wings 4, 5 is electrically connected to the contact element 7. Both connecting pieces 8, 9, which are shown only schematically, serve respectively to connect a measurement line for connecting the butterfly cannula to the monitoring unit of the device for monitoring the vessel access, which will be described in more detail below.

In the following, the method of functioning of the monitoring device according to the invention will be explained in detail, with reference to FIGS. 3 and 4 as well as 5A to 5C.

The measurement principle is based on measuring the impedance of the patient between the puncture cannula 1 and the contact element 7, which rests on the patient's skin, on the upper arm.

Figure 3:
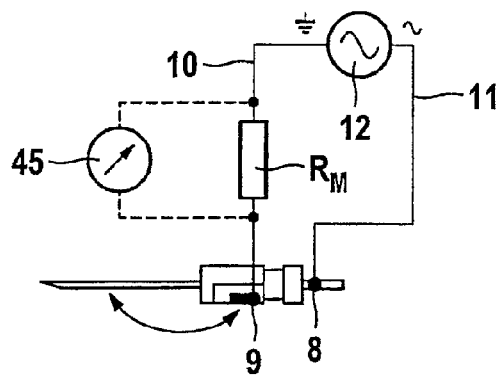
FIG. 3 shows a circuit arrangement to illustrate the functional principle of the device according to the invention, for monitoring the vessel access.

FIG. 3 shows a circuit arrangement to illustrate the measurement principle. The two connections 8, 9 of the butterfly cannula are connected via measurement lines 10, 11 to a frequency generator 12, which supplies an AC voltage signal. A precision resistor $R_M$ is connected into one of the two measurement lines.

With an oscilloscope 45, the voltage that drops at the precision resistor $R_M$ is measured. It is assumed here that an electrical connection is effected by the patient between the two connecting pieces 8, 9. In the event of a disconnection or dislocation of the puncture needle, the impedance consequently changes, which is demonstrated by a decrease in the amplitude of the signal measured with the oscilloscope 45.

Figure 4:
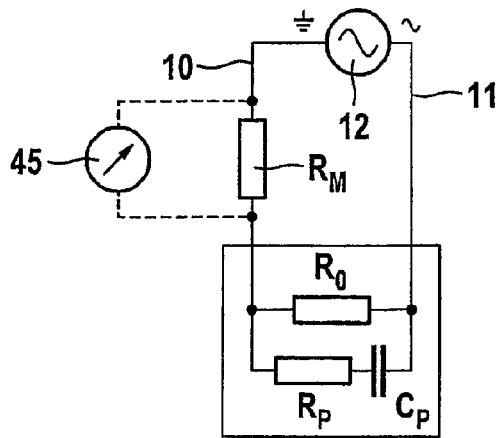
FIG. 4 shows the equivalent circuit diagram of the circuit arrangement of FIG. 3.

FIG. 4 shows an equivalent circuit diagram of the conductive connection that is effected via the patient between the connecting pieces 8, 9 of the butterfly cannula. The equivalent circuit diagram of the "patient" is the parallel connection of a series connection of a resistor $R_P$ and a capacitor $C_P$ on the one hand and a resistor $R_0$ on the other hand.

FIGS. 5A to 5C show the position of the butterfly cannula and the voltage signal measured with the oscilloscope.

If the patient access is correct (FIG. 5A), i.e. if the puncture needle is located in the vessel 13 of the patient and the contact element 7 lies on the skin 14 of the patient, an AC voltage signal of relatively large amplitude is measured. The AC voltage signal that is measured is shown in the right-hand half of the picture in FIG. 5A.

In the event of a dislocation of the butterfly cannula, i.e. if the puncture needle is still in the vessel 13 but the base body 2 with the contact element 7 no longer lies on the skin 14 of the patient (FIG. 5B), an AC voltage signal of a lower amplitude is measured. The AC voltage signal that is measured is shown in the right-hand half of the picture in FIG. 5B.

In the event of a disconnection, i.e. if the puncture needle has slipped out of the vessel 13, the signal as shown in the right-hand half of the picture in FIG. 5C is measured. The signal once again has a considerably lower amplitude than that measured in the case of correct vessel access (FIG. 5A). The amplitude of the measured signal is considerably lower even if the contact element 7 of the base body 2 is still resting against the skin 14 of the patient.

Consequently, by comparing the amplitude of the measured AC voltage signal with specified threshold values, one can reliably detect whether patient access is correct or not.

Figure 2:
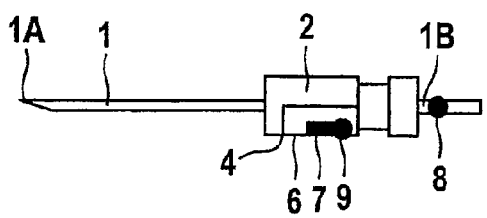
FIG. 2 shows the device for producing a vessel access from FIG. 1, in side view.
Figure 6:
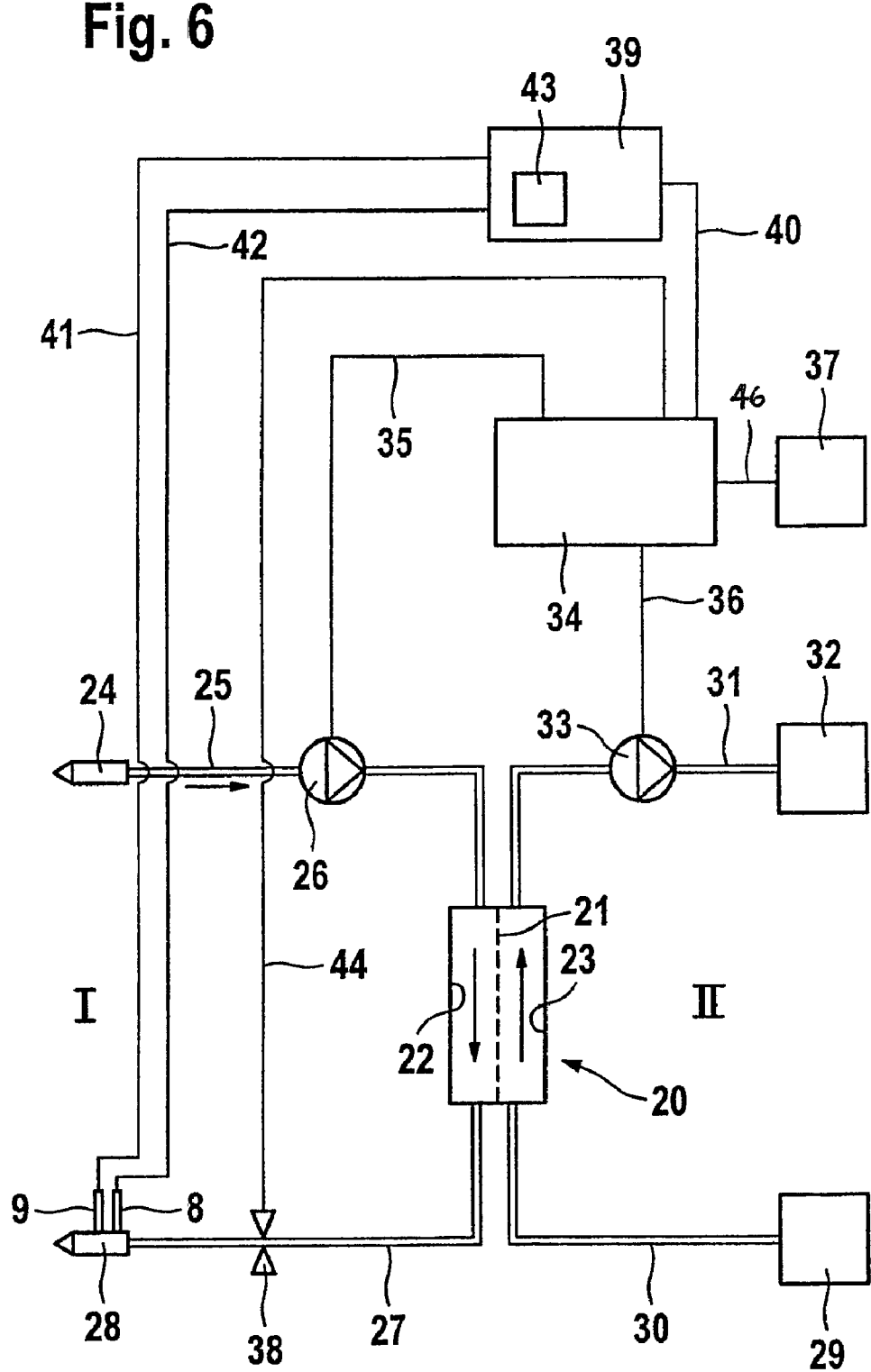
FIG. 6 shows the significant components of an extracorporeal blood treatment device according to the invention, with a device according to the invention for monitoring vessel access.

Described below is the extracorporeal blood treatment device according to this invention, which has a device for monitoring the vessel access. FIG. 6 shows only the significant components of the blood treatment system in schematic representation, as the person skilled in the art will be familiar with blood treatment devices as such. The device for producing vessel access, which is described with reference to the FIGS. 1 and 2, is likewise shown only schematically in FIG. 6.

The blood treatment device is a familiar hemodialysis device, which has a dialyzer 20 that is divided by a semi-permeable membrane 21 into a blood chamber 22 and a hemodialysis solution chamber 23.

The patient's blood is taken by means of a first device for producing a vessel access 24 (butterfly cannula), and is supplied to the inlet of the blood chamber 22 of the dialyzer 20 via an arterial blood line 25 into which a blood pump 26 is connected and which is connected to the butterfly cannula 24. A venous blood line 27 goes out from the blood chamber 22 of the dialyzer 20 and leads to the venous butterfly cannula 28. The blood pump 26 conveys the patient's blood in the extracorporeal circuit I of the dialysis machine.

The hemodialysis solution circuit II of the dialysis machine comprises a hemodialysis solution source 29, connected to which is a hemodialysis solution supply line 30, which leads to the inlet of the hemodialysis solution chamber 23 of the dialyzer 20. Going out from the outlet of the hemodialysis solution chamber 23 of the dialyzer is a hemodialysis solution drain line 31 which leads to an outlet 32. A hemodialysis solution pump 33 is connected into the hemodialysis solution drain line 31.

Control of the dialysis machine is undertaken by a central control unit 34, which triggers the blood pump 26 and hemodialysis solution pump 33 via control lines 35, 36. The central control unit 34 is connected via a data line 46 to an alarm unit 37, which emits an optical and/or acoustic alarm in the event of a fault.

Downstream of the blood chamber 22 of the dialyzer 20, on the venous tube conduit 27, is a hose clamp 38 which can be operated electromagnetically, and which is closed by the central control unit 34 via a further control line 44 if the venous puncture needle 28 should slip out of the vessel access. Furthermore, after the needle has slipped out, the control unit 34 stops the blood pump 26.

In general, the components described above are already present in the familiar dialysis devices.

Besides the device according to the invention for producing the venous vessel access 28 (butterfly cannula), the device according to the invention for monitoring the vessel access comprises a monitoring unit 39, which communicates with the central control unit 34 of the dialysis machine via a further data line 40. The monitoring unit 39 is connected via two measurement lines 41, 42 to butterfly cannulas 24, 28, wherein the two measurement lines 41, 42 are connected to their connecting pieces 8, 9. The monitoring unit 39 carries out a measurement of impedance, described with reference to FIGS. 3 and 4, wherein the amplitude of a voltage signal dropping at a precision resistor is measured. The monitoring unit 39 has a comparison unit 43, with which the measured voltage signal is compared to a specified threshold value. If the measured value falls below the threshold value, the monitoring unit 39 produces an alarm signal which is transmitted via the data line 40 to the central control unit 34. The central control unit 34 thereupon triggers the alarm unit 37, which emits an optical and/or acoustic alarm. Furthermore, the control unit 34 triggers the hose clamp 38, which interrupts the venous tube conduit 27.

In an alternative embodiment, the measured impedance is compared to a lower threshold value as well as to an upper threshold value, which define a tolerance range. If the impedance lies within the tolerance range, i.e. if the impedance is less than the upper threshold value and greater than the lower threshold value, correct vessel access is assumed. By contrast, if the impedance is outside the tolerance range, it is assumed that the vessel access is incorrect.

The monitoring device according to the present invention, which makes use of the device according to the present invention for producing a vessel access (butterfly cannula), is characterized in that a disconnection or dislocation can be detected even if the tube system is not filled with blood, but there is air in the venous tube conduit.

The invention claimed is:

1. A device for monitoring vessel access for extracorporeal blood treatment comprising:
   an electrically conductive puncture needle having a proximal end piece and a distal end piece for inserting into a blood vessel;
   a base body of electrically non-conductive material having a proximal end, a distal end, a central retainer piece having a lumen, and two wings projecting from the central retainer piece, said base body receiving the puncture needle within the lumen;
   an electrically conductive contact element located on a bottom surface of the base body and adapted to contact the patient's skin;
   a first connecting piece electrically connected to the puncture needle and adapted to connect to a first measurement line; and
   a second connecting piece electrically connected to the contact element on the base body and adapted to connect to a second measurement line.

2. The device of claim 1, wherein the contact element is located on a bottom surface of at least one of the two wings.

3. The device of claim 1, wherein the contact element is located on a bottom surface of the central retainer piece.

4. The device of claim 1, further comprising:
a monitoring unit connected to the first connecting piece and the second connecting piece, said monitoring unit configured to measure the impedance between the puncture needle and the contact element and determine an incorrect vessel access if the impedance lies outside a specified range.

5. The device of claim 4, further comprising:
the first measurement line connecting the monitoring unit to the first connecting piece; and
the second measurement line connecting the monitoring unit to the second connecting piece.

6. The device of claim 4, said monitoring unit comprising a comparison unit configured to compare the measured impedance to a specified lower threshold value, wherein incorrect vessel access is determined if the measured value falls below the lower threshold value.

7. The device of claim 4, said monitoring unit comprising a comparison unit configured to compare the measured impedance to a specified upper threshold value, wherein incorrect vessel access is determined if the measured value exceeds the upper threshold value.

8. The device of claim 6, said comparison unit further configured to compare the measured impedance to a specified upper threshold value, wherein incorrect vessel access is determined if the measured value exceeds the upper threshold value.

9. The device of claim 1, wherein the puncture needle comprises a conductive polymer.

10. The device of claim 1, wherein the two wings are flexible.

11. The device of claim 1, wherein said puncture needle forms a first measurement electrode and said contact element forms a second measurement electrode.

12. The device of claim 1, wherein the proximal end piece of the puncture needle extends proximally from the proximal end of the base body and the distal end piece of the puncture needle extends distally from the distal end of the base body.

13. The device of claim 1, wherein the electrically conductive contact element comprises a layer of electrically conductive material.

14. The device of claim 2, wherein a layer of electrically conductive material extends over the entire bottom surface of the two wings.

15. An extracorporeal blood treatment device comprising the device for monitoring vessel access of claim 1.

16. A method for monitoring a vessel access in extracorporeal blood treatment comprising:
inserting a device for creating vessel access into a patient's vessel, said device comprising:
an electrically conductive puncture needle having a proximal end piece and a distal end piece, said puncture needle forming a first measurement electrode;
a base body of electrically non-conductive material, said base body having a proximal end, a distal end, a central retainer piece having a lumen, and two wings projecting from the central retainer piece; and
an electrically conductive contact element located on a bottom surface of at least one of the two wings or the central retainer piece and adapted to contact the patient's skin, said contact element forming a second measurement electrode,
wherein the puncture needle is received within the lumen of the base body;
measuring the impedance between the puncture needle and the contact element on the base body; and
determining there is incorrect vessel access if the measured impedance lies outside a specified range.

17. The method of claim 16, wherein the specified range comprises a lower threshold value, further comprising:
comparing the measured impedance to the lower threshold value; and
determining that there is incorrect vessel access if the measured value falls below the lower threshold value.

18. The method of claim 16, wherein the specified range comprises an upper threshold value, further comprising:
comparing the measured impedance to the upper threshold value,
determining that there is incorrect vessel access if the measured value exceeds the upper threshold value.

19. The method of claim 16, wherein the proximal end piece of the puncture needle extends proximally from the proximal end of the base body and the distal end piece of the puncture needle extends distally from the distal end of the base body, said method further comprising:
electrically connecting a first connecting piece to the puncture needle and to a first measurement line; and
electrically connecting a second connecting piece to the contact element on the base body and to a second measurement line.

20. The method of claim 16, wherein the impedance is measured during extracorporeal blood treatment.

21. The method of claim 16, wherein measuring the impedance comprises:
measuring the amplitude of a voltage signal dropping at a precision resistor.

22. The method of claim 21, wherein determining there is incorrect vessel access if the measured impedance lies outside a specified range comprises:
comparing the measured voltage signal to a specified threshold value.

* * * * *